United States Patent
Hayashi

(10) Patent No.: US 11,607,110 B2
(45) Date of Patent: Mar. 21, 2023

(54) ELECTRONIC ENDOSCOPE PROCESSOR AND ELECTRONIC ENDOSCOPE SYSTEM

(71) Applicant: HOYA CORPORATION, Tokyo (JP)

(72) Inventor: Yoshihiro Hayashi, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 476 days.

(21) Appl. No.: 16/300,225

(22) PCT Filed: Aug. 25, 2017

(86) PCT No.: PCT/JP2017/030629
§ 371 (c)(1),
(2) Date: Nov. 9, 2018

(87) PCT Pub. No.: WO2018/038269
PCT Pub. Date: Mar. 1, 2018

(65) Prior Publication Data
US 2019/0142240 A1    May 16, 2019

(30) Foreign Application Priority Data
Aug. 25, 2016   (JP) .............................. JP2016-164990

(51) Int. Cl.
*A61B 1/00*       (2006.01)
*A61B 1/05*       (2006.01)
(Continued)

(52) U.S. Cl.
CPC .... *A61B 1/000095* (2022.02); *A61B 1/00006* (2013.01); *A61B 1/045* (2013.01);
(Continued)

(58) Field of Classification Search
CPC . A61B 1/00006; A61B 1/0646; A61B 1/0653; A61B 1/00009; A61B 1/045;
(Continued)

(56) References Cited

U.S. PATENT DOCUMENTS 5,187,572 A * 2/1993 Nakamura ........... H04N 5/2354
                                                        348/E5.029
2004/0267091 A1   12/2004 Imaizumi et al.
(Continued)

FOREIGN PATENT DOCUMENTS

CN    1572230 A    2/2005
EP    1488732 A1   12/2004
(Continued)

OTHER PUBLICATIONS

U.S. Appl. No. 16/098,043 to Shinya Shimotashiro et al., which was filed on Oct. 31, 2018.
(Continued)

*Primary Examiner* — John P Leubecker
(74) *Attorney, Agent, or Firm* — Greenblum & Bernstein, P.L.C.

(57) ABSTRACT

An electronic endoscope processor for processing an image signal of a subject imaged using an imaging element in an electronic endoscope system includes: an illuminating light switch that alternatingly switches the illuminating light to be emitted to the subject, between a first illuminating light and a second illuminating light; and an imaging element control circuit that controls an exposure time of the imaging element and a charge readout timing. The imaging element control circuit controls the exposure time T1 of the imaging element when the first illuminating light is being emitted to the subject and the exposure time T2 of the imaging element when the second illuminating light is being emitted to the subject, based on a time-integrated amount of luminous flux per unit time of the first illuminating light and a time-integrated amount of luminous flux per unit time of the second illuminating light.

6 Claims, 7 Drawing Sheets

(51) Int. Cl.
  *A61B 1/06* (2006.01)
  *A61B 1/045* (2006.01)
  *G02B 23/24* (2006.01)
  *A61B 1/07* (2006.01)
(52) U.S. Cl.
  CPC .............. *A61B 1/05* (2013.01); *A61B 1/0669* (2013.01); *A61B 1/07* (2013.01); *G02B 23/24* (2013.01); *A61B 1/0655* (2022.02)
(58) Field of Classification Search
  CPC ....... A61B 1/05; A61B 1/0669; A61B 1/0661; A61B 1/06–07; G02B 23/24; G06T 1/0007; G06T 1/00; G06T 2207/30004
  See application file for complete search history.

(56) References Cited

U.S. PATENT DOCUMENTS

| | | |
|---|---|---|
| 2005/0117028 A1 | 6/2005 | Imaizumi et al. |
| 2015/0092034 A1 | 4/2015 | Iwane |
| 2017/0000393 A1 | 1/2017 | Hayashi et al. |
| 2017/0085763 A1* | 3/2017 | Sakai .................. H04N 5/2256 |
| 2018/0064319 A1 | 3/2018 | Hayashi |

FOREIGN PATENT DOCUMENTS

| | | |
|---|---|---|
| EP | 1527730 A1 | 5/2005 |
| EP | 2862500 A | 4/2015 |
| JP | 2005-006768 A | 1/2005 |
| JP | 2005-033282 A | 2/2005 |
| JP | 2005-131129 A | 5/2005 |
| JP | 2010-068992 A | 4/2010 |
| JP | 2015-066063 A | 4/2015 |
| JP | 2016-123755 A | 7/2016 |
| WO | WO2010/131620 A1 | 11/2010 |
| WO | WO2013/146311 A1 | 10/2013 |
| WO | WO2016/056388 A1 | 4/2016 |

OTHER PUBLICATIONS

International Search Report issued in International Patent Application No. PCT/JP2017/030629, dated Nov. 14, 2017, along with an English translation thereof.

Office Action issued in Japanese family member Patent Appl. No. 2018-535793, dated Jan. 7, 2020.

* cited by examiner

ELECTRONIC ENDOSCOPE PROCESSOR AND ELECTRONIC ENDOSCOPE SYSTEM

TECHNICAL FIELD

The present invention relates to an electronic endoscope processor and an electronic endoscope system.

BACKGROUND ART

In the medical device field, an electronic endoscope is known which facilitates diagnosis of a lesion portion by simultaneously performing observation using illuminating lights of wavelength regions with different characteristics. For example, a specific configuration of this type of electronic endoscope system is described in Patent Document 1.

Patent Document 1 discloses an electronic endoscope system in which a subject is alternatingly illuminated with white normal light and special light with a wavelength band different from that of the normal light, and object light from the subject is detected with a CMOS-type image sensor. A rolling shutter method is employed in the CMOS-type image sensor, and exposure of pixels and readout of pixel signals are performed sequentially line by line. For this reason, when the subject is alternatingly illuminated by the normal light and the special light, the information of the subject when illuminated by the normal light and the information of the subject when illuminated by the special light are mixed together in the pixel signal. With the electronic endoscope system disclosed in Patent Document 1, in order to prevent the information of the subject illuminated by the different illuminating lights being mixed together in the pixel signal, the illuminating light is turned off every other frame and the pixel signal is read out while the illuminating light is turned off.

CITATION LIST

Patent Documents

Patent Document 1: JP 2010-068992A

SUMMARY OF INVENTION

Technical Problem

As with the electronic endoscope system according to Patent Document 1, when the subject is alternatingly illuminated with normal light and special light, a difference occurs in some cases between the illumination level of the subject illuminated by the normal light and the illumination level of the subject illuminated by the special light. In the case where the difference in the illumination levels of two subjects is large, if exposure correction is performed in accordance with one of the subject images, a problem occurs in which the other subject image is overexposed or underexposed.

The present invention was made in view of the foregoing circumstance and it is an object thereof to provide an electronic endoscope processor and an electronic endoscope system in which in the case of observing a subject using illuminating lights with different light amounts, the subject illuminated with either light can be imaged with the correct exposure.

Solution to the Problem

An electronic endoscope processor according to an embodiment of the present invention includes: an illuminating light switching means for alternatingly switching illuminating light to be emitted to a subject, between a first illuminating light and a second illuminating light with a different time-integrated amount of luminous flux per unit time from the first illuminating light; and an imaging element control means for controlling an exposure time of the imaging element and a charge readout timing. In this configuration, the imaging element control means controls an exposure time $T1$ of the imaging element when the first illuminating light is being emitted to the subject and an exposure time $T2$ of the imaging element when the second illuminating light is being emitted to the subject, based on a time-integrated amount $R1$ of luminous flux per unit time of the first illuminating light and a time-integrated amount $R2$ of luminous flux per unit time of the second illuminating light.

Here, according to a later-described embodiment, the illuminating light switching means includes a rotating filter portion 260.

According to a later-described embodiment, the imaging element control means is a circuit of a system controller 202, a timing controller 204, or a driver signal processing circuit 110. According to an embodiment, the imaging element control means controlling the exposure time of the imaging element and the charge readout timing means that the system controller 202, which is at least a portion of these circuits, is configured to generate a control signal for controlling the exposure time and the charge readout timing, and transmit the control signal to the imaging element via the timing controller 204 and the driver signal processing circuit 110. It means that the imaging element is configured to receive the control signal and perform operation corresponding to the control signal in accordance with the control signal. The above-described content also applies to the later-described illuminating light switching means and the imaging element control means.

According to this kind of configuration, if the first illuminating light and the second illuminating light, which have different light amounts (time-integrated amount of luminous flux per unit time) are alternatingly emitted to the subject, the exposure time of the imaging element is adjusted according to the light amount of the illuminating light emitted to the subject. For this reason, both the subject illuminated by the first illuminating light and the subject illuminated by the second illuminating light can be imaged with the correct exposure.

Also, according to an embodiment of the present invention, it is preferable that, for example, the imaging element control means adjusts the exposure time $T1$ and the exposure time $T2$ such that $T1 \times R1 = T2 \times R2$ is satisfied.

Also, according to an embodiment of the present invention, for example, an electronic endoscope including the imaging element is attachable to and detachable from the electronic endoscope processor. In this configuration, it is preferable that the imaging element control means acquires an amplification factor for amplification processing implemented on the image signal in at least one of the electronic endoscope and the electronic endoscope processor, and if the amplification factor of amplification processing implemented on the image signal of the subject to which the first light was emitted is defined as $G1$ and the amplification factor of amplification processing implemented on the image signal of the subject to which the second light was emitted is defined as $G2$, the imaging element control means adjusts the exposure time $T1$ and the exposure time $T2$ such that $T1 \times R1 \times G1 = T2 \times R2 \times G2$ is satisfied.

Here, the imaging element control means acquiring the amplification factor for the amplification processing implemented on the image signal means that in a later-described embodiment, the circuit corresponding to the imaging element control means reads out and acquires the information of the amplification factor stored in the memory 112 of the electronic endoscope.

According to a later-described embodiment, part of the circuit corresponding to the imaging element control means or the signal processing circuit 220 is configured to perform the amplification processing. Accordingly, according to a later-described embodiment, part of the circuit corresponding to the imaging element control means is configured to also adjust the amplification factor.

Also, in an embodiment of the present invention, for example, the time for which the first illuminating light is continuously emitted to the subject and the time for which the second illuminating light is continuously emitted to the subject are equal.

Also, according to an embodiment of the present invention, it is preferable that, for example, the illuminating light switching means includes: a light source configured to emit white light; a rotating plate in which a first filter configured to filter the white light into the first illuminating light and a second filter configured to filter the white light into the second illuminating light are arranged side by side in approximately the same angle range in a circumferential direction; and a rotation drive unit configured to, by rotating the rotating plate, insert the first filter into an optical path of the white light in an emission period of the first illuminating light, and insert the second filter into the optical path in an emission period of the second illuminating light.

Also, according to an embodiment of the present invention, it is preferable that, for example, the illuminating light switching means sequentially switches the illuminating light emitted to the subject between the first illuminating light, the second illuminating light, and a third illuminating light that has a time-integrated amount of luminous flux per unit time that is different from those of the first illuminating light and the second illuminating light. In this case, it is preferable that the imaging element control means controls the exposure time T1, the exposure time T2, and an exposure time T3 of the imaging element when the third illuminating light is being emitted to the subject, based on the time-integrated amount R1, the time-integrated amount R2, and a time-integrated amount R3 of luminous flux per unit time of the third illuminating light.

An electronic endoscope system according to an embodiment of the present invention includes: an illuminating light switching means for alternatingly switching illuminating light to be emitted to a subject, between a first illuminating light and a second illuminating light with a different time-integrated amount of luminous flux per unit time from the first illuminating light; an imaging element configured to receive light from the subject and output an image signal corresponding to the received light; and an imaging element control means for controlling an exposure time of the imaging element and a charge readout timing. In this configuration, the imaging element control means controls an exposure time T1 of the imaging element when the first illuminating light is being emitted to the subject and an exposure time T2 of the imaging element when the second illuminating light is being emitted to the subject, based on a time-integrated amount R1 of luminous flux per unit time of the first illuminating light and a time-integrated amount R2 of luminous flux per unit time of the second illuminating light.

Also, according to an embodiment of the present invention, it is preferable that, for example, the imaging element control means adjusts the exposure time T1 and the exposure time T2 such that $T1 \times R1 = T2 \times R2$ is satisfied.

An electronic endoscope system according to an embodiment of the present invention includes: an electronic endoscope processor including the illuminating light switching means and the imaging element control means; and an electronic endoscope that includes the imaging element and is configured to be detachably connected to the electronic endoscope processor.

The electronic endoscope processor or the electronic endoscope includes: an amplification means for implementing amplification processing on the image signal output from the imaging element; and a control means for controlling an amplification factor for the amplification processing.

A first wavelength band of the first illuminating light and a second wavelength band of the second illuminating light are mutually different.

In this case, it is preferable that the control means controls the amplification factor implemented on the image signal of the subject that received emission of at least one of the first illuminating light and the second illuminating light, based on a calculation amount K1 relating to the first illuminating light in the first wavelength band, a calculation amount K2 relating to the second illuminating light in the second wavelength band, and the exposure times T1 and T2, the calculation amount K1 being an amount obtained by integrating a product of a light intensity distribution of the first illuminating light in the first wavelength band and a distribution of quantum efficiency of the imaging element in the first wavelength band, in the range of the first wavelength band, and the calculation amount K2 being an amount obtained by integrating a product of a light intensity distribution of the second illuminating light in the second wavelength band and a distribution of quantum efficiency of the imaging element in the second wavelength band, in the range of the second wavelength band.

According to a later-described embodiment, the control means preferably includes a driver signal processing circuit 110 or a system controller 202. According to a later-described embodiment, the amplification means includes the driver signal processing circuit 110 or the upstream signal processing circuit 220. The control means controlling the amplification factor means that at least part of these circuits are configured to generate a control signal for setting the amplification factor and transmit the control signal to the circuit corresponding to the amplification means. This means that the circuit corresponding to the amplification means is configured to receive the control signal and to operate in accordance with the control signal. The above-described content also applies to the later-described control means and the amplification means.

According to an embodiment of the present invention, it is preferable that if the amplification factors implemented on the image signal of the subject that received the emission of the first illuminating light and the second illuminating light are defined as G3 and G4 respectively and the exposure times of the imaging element when the first illuminating light and the second illuminating light are emitted are defined as T3 and T4 respectively, the control means controls the amplification factors G3 and G4 based on $G3 \times T3 \times K1 = G4 \times T4 \times K2$.

Also, according to an embodiment of the present invention, for example, the electronic endoscope system further includes: an electronic endoscope processor including the illuminating light switching means and the imaging element control means; an electronic endoscope that includes the imaging element and is detachably connected to the electronic endoscope processor; and an amplification means for implementing amplification processing on the image signal output from the imaging element. In this configuration, it is preferable that the amplification means implements the amplification processing at an amplification factor G1 on the image signal of the subject to which the first illuminating light was emitted, and the amplification means implements the amplification processing at an amplification factor G2 on the image signal of the subject to which the second illuminating light was emitted. Also, it is preferable that the imaging element control means adjusts the exposure time T1 and the exposure time T2 such that $T1 \times R1 \times G1 = T2 \times R2 \times G2$ is satisfied.

According to an embodiment of the present invention, it is preferable that the wavelength band of the first illuminating light and the wavelength band of the second illuminating light are mutually different, and if average quantum efficiencies of the imaging element in the wavelength bands of the first illuminating light and the second illuminating light are defined as AQE1 and AQE2 respectively, the imaging element control means adjusts the exposure time T1 and the exposure time T2 such that $T1 \times R1 \times AQE1 = T2 \times R2 \times AQE2$ is satisfied.

According to an embodiment of the present invention, it is preferable that an electronic endoscope including the imaging element is attachable to and detachable from the electronic endoscope system, the wavelength band of the first illuminating light and the wavelength band of the second illuminating light are mutually different, and the imaging element control means acquires an amplification factor for amplification processing implemented on the image signal in at least one of the electronic endoscope and the electronic endoscope processor, and if the amplification factor of amplification processing implemented on the image signal of the subject to which the first light was emitted is defined as G1, the amplification factor of amplification processing implemented on the image signal of the subject to which the second light was emitted is defined as G2, and furthermore, the average quantum efficiencies of the imaging element in the wavelength bands of the first illuminating light and the second illuminating light are defined as AQE1 and AQE2 respectively, the imaging element control means adjusts the exposure time T1 and the exposure time T2 such that $T1 \times R1 \times AQE1 \times G1 = T2 \times R2 \times AQE2 \times G2$ is satisfied.

An electronic endoscope system according to an embodiment of the present invention includes:

an illuminating light switching means for alternatingly switching illuminating light to be emitted to a subject, between a first illuminating light and a second illuminating light with a different time-integrated amount of luminous flux per unit time from the first illuminating light;

an imaging element configured to receive light from the subject and output an image signal corresponding to the received light; and an imaging element control means for controlling an exposure time of the imaging element and a charge readout timing.

The imaging element control means controls the exposure time T1 of the imaging element when the first illuminating light is being emitted to the subject and the exposure time T2 of the imaging element when the second illuminating light is being emitted to the subject, based on a calculation amount K1 relating to the first illuminating light in the first wavelength band and a calculation amount K2 relating to the second illuminating light in the second wavelength band, the calculation amount K1 being an amount obtained by integrating a product of a light intensity distribution of the first illuminating light in the first wavelength band and a distribution of quantum efficiency of the imaging element in the first wavelength band, in the range of the first wavelength band, and the calculation amount K2 being an amount obtained by integrating a product of a light intensity distribution of the second illuminating light in the second wavelength band and a distribution of quantum efficiency of the imaging element in the second wavelength band, in the range of the second wavelength band.

According to an embodiment of the present invention, it is preferable that the imaging element control means controls the exposure times T1 and T2 such that $T1 \times K1 = T2 \times K2$ is satisfied.

An electronic endoscope system according to an embodiment of the present invention includes:

an illuminating light switching means for alternatingly switching illuminating light to be emitted to a subject, between a first illuminating light and a second illuminating light with a different time-integrated amount of luminous flux per unit time from the first illuminating light;

an imaging element configured to receive light from the subject and output an image signal corresponding to the received light;

an imaging element control means for controlling an exposure time of the imaging element and a charge readout timing, and controlling the imaging element such that the subject to which the first illuminating light was emitted is imaged with an exposure time T3 and the subject to which the second illuminating light was emitted is imaged with an exposure time T4;

an amplification means for implementing amplification processing on the image signal output from the imaging element; and a control means for controlling an amplification factor of the amplification processing.

A first wavelength band of the first illuminating light and a second wavelength band of the second illuminating light are mutually different, the control means controls the amplification factor implemented on the image signal of the subject that received emission of one of the first illuminating light and the second illuminating light, based on the amplification factor implemented on the image signal of the subject that received emission of the other illuminating light, a calculation amount K1 relating to the first illuminating light in the first wavelength band, a calculation amount K2 relating to the second illuminating light in the second wavelength band, and the exposure times T3 and T4, the calculation amount K1 being an amount obtained by integrating a product of a light intensity distribution of the first illuminating light in the first wavelength band and a distribution of quantum efficiency of the imaging element in the first wavelength band, in the range of the first wavelength band, and the calculation amount K2 being an amount obtained by integrating a product of a light intensity distribution of the second illuminating light in the second wavelength band and a distribution of quantum efficiency of the imaging element in the second wavelength band, in the range of the second wavelength band.

According to an embodiment of the present invention, it is preferable that if the amplification factors implemented on the image signal of the subject that received the emission of the first illuminating light and the second illuminating light are defined as G3 and G4 respectively and the exposure times of the imaging element when the first illuminating light and the second illuminating light are emitted are defined as T3 and T4, the control means controls the amplification factors G3 and G4 based on G3×T3×K1=G4×T4×K2.

According to an embodiment of the present invention, it is preferable that the imaging element is configured to read out the charges at the light receiving positions while shifting the timings of starting and ending exposure at the light receiving positions on the light receiving surface of the imaging element, the light intensity of the first illuminating light is higher than the light intensity of the second illuminating light, the exposure time T2 is less than or equal to a reference time obtained by dividing the time for which the second illuminating light is emitted to the subject by the number of instances of reading out the charges at the light receiving positions, and is greater than or equal to an amount of time obtained by subtracting the charge readout time and a reset time for resetting noise accumulation charges prior to the exposure at the light receiving positions from the reference time.

According to an embodiment of the present invention, it is preferable that a minimum time for shifting in the light receiving positions of the timings for starting and stopping the exposure of the imaging element is equal to the reset time.

According to an embodiment of the present invention, it is preferable that the second illuminating light has a transition period in which light intensity gradually increases along with time from the start of emission, before the light intensity becomes constant, and the period for resetting the noise accumulation charges, performed before the charge readout, which is performed first in the emission time, is within the transition period.

Also, according to an embodiment of the present invention, it is preferable that, for example, the time for which the first illuminating light is continuously emitted to the subject and the time for which the second illuminating light is continuously emitted to the subject are equal.

Also, according to an embodiment of the present invention, for example, the illuminating light switching means preferably includes: a light source configured to emit white light; a rotating plate in which a first filter configured to filter the white light into the first illuminating light and a second filter configured to filter the white light into the second illuminating light are arranged side by side in approximately the same angle range in a circumferential direction; and a rotation drive unit configured to, by rotating the rotating plate, insert the first filter into an optical path of the white light in an emission period of the first illuminating light, and insert the second filter into the optical path in an emission period of the second illuminating light.

Also, according to an embodiment of the present invention, for example, the illuminating light switching means preferably sequentially switches the illuminating light emitted to the subject between the first illuminating light, the second illuminating light, and a third illuminating light that has a time-integrated amount of luminous flux per unit time that is different from those of the first illuminating light and the second illuminating light. In this case, it is preferable that the imaging element control means controls the exposure time T1, the exposure time T2, and an exposure time T3 of the imaging element when the third illuminating light is being emitted to the subject, based on the time-integrated amount R1, the time-integrated amount R2, and a time-integrated amount R3 of luminous flux per unit time of the third illuminating light.

An electronic endoscope system according to an embodiment of the present invention includes:

An illuminating light switching means for alternatingly switching illuminating light to be emitted to a subject, between a first illuminating light in a first wavelength band and a second illuminating light in a second wavelength band different from the first wavelength band, the second illuminating light having a time-integrated amount of luminous flux per unit time that is different from that of the first illuminating light; and an imaging element configured to receive light from the subject and output an image signal corresponding to the received light.

The exposure time T1 of the imaging element when the first illuminating light is being emitted to the subject and the exposure time T2 of the imaging element when the second illuminating light is being emitted to the subject satisfy T1×K1=T2×K2.

The K1 is an amount obtained by integrating a product of a light intensity distribution of the first illuminating light in the first wavelength band and a distribution of quantum efficiency of the imaging element in the first wavelength band, in the range of the first wavelength band, and the K2 is an amount obtained by integrating a product of a light intensity distribution of the second illuminating light in the second wavelength band and a distribution of quantum efficiency of the imaging element in the second wavelength band, in the range of the second wavelength band).

Also, according to an embodiment of the present invention, for example, the imaging element is preferably a CMOS-type image sensor.

Advantageous Effects of the Invention

According to the above-described electronic endoscope processor and the electronic endoscope system, in the case of observing a subject using illuminating lights with different light amounts, the subject illuminated with either illuminating light can be imaged with the correct exposure.

DESCRIPTION OF EMBODIMENTS

Hereinafter, embodiments of the present invention will be described with reference to the drawings. Note that in the following description, in an embodiment of the present invention, an electronic endoscope system is described as an example. Note that "controlling" or "adjusting" the exposure time or the amplification factor (gain) in the description below encompasses a case of performing a control operation or adjustment operation, as well as the exposure time or the amplification factor being set to a value resulting from control or a value resulting from adjustment.

Figure 1:
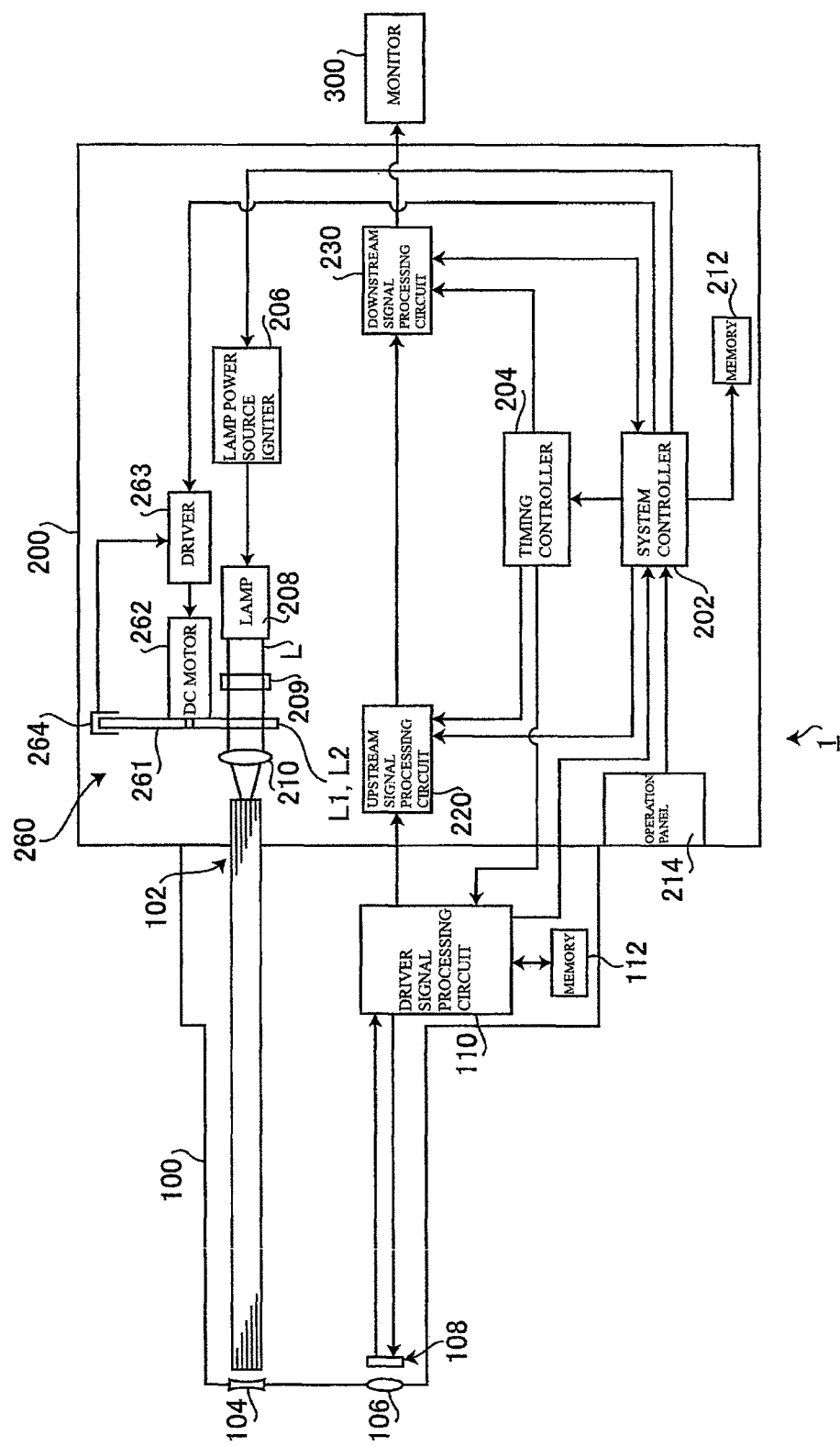
FIG. 1 is a block diagram showing a configuration of an electronic endoscope system according to an embodiment of the present invention.

FIG. 1 is a block diagram showing a configuration of an electronic endoscope system 1 according to an embodiment of the present invention. As shown in FIG. 1, the electronic endoscope system 1 includes an electronic endoscope 100, a processor 200, and a monitor 300.

The processor 200 includes a system controller 202 and a timing controller 204. The system controller 202 executes various types of programs stored in a memory 212 and performs overall control of the electronic endoscope system 1. Also, the system controller 202 is connected to an operation panel 214. In response to an instruction from an operator input through the operation panel 214, the system controller 202 changes the operations of the electronic endoscope system 1 and changes the parameters of the operations. The timing controller 204 outputs a clock pulse for adjusting the timing of the operations of the units to the circuits in the electronic endoscope system 1.

A lamp 208 emits an illuminating light L after being started using a lamp power source igniter 206. For example, the lamp 208 is a high-luminance lamp, such as a xenon lamp, a halogen lamp, a mercury lamp, or a metal-halide lamp. Also, the lamp 208 may be a solid-state light source such as an LED (light emitting diode), or a laser diode. The illuminating light L is light having a spectrum spreading mainly from the visible light region to the infrared light region, which is not visible (or white light including at least the visible light region).

Figure 2:
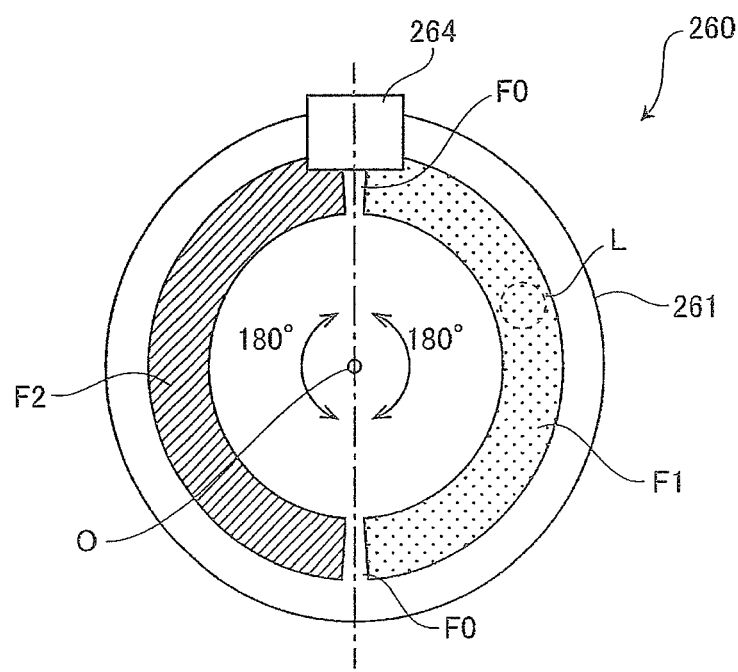
FIG. 2 is a front view of a rotating filter portion provided in a processor according to an embodiment of the present invention.

The light amount of the illuminating light L emitted by the lamp 208 is narrowed down by the aperture 209, and thereafter the illuminating light L is incident on the rotating filter portion 260. FIG. 2 is a front view from a condensing lens 210 side of the rotating filter portion 260. The rotating filter portion 260 includes a rotary turret 261, a DC motor 262, a driver 263, and a photointerrupter 264. In FIG. 2, the illuminating light L incident on the rotary turret 261 is indicated by a broken line. As shown in FIG. 2, a normal light (white light) optical filter F1 and a special light optical filter F2 are sequentially arranged side by side in the rotary turret 261. The optical filters F1 and F2 are fan-shaped and are arranged in approximately 180-degree angle ranges around a rotational shaft O.

The driver 263 drives the DC motor 262 under control by the system controller 202. The optical filters F1 and F2 are sequentially inserted into the optical path of the illuminating light L due to the rotary turret 261 performing a rotation operation due to the DC motor 262. Thus, the illuminating light L incident from the lamp 208 is filtered by the optical filters, and one of two types of the illuminating light (normal light L1 and special light L2) with different spectra is emitted at a timing in synchronization with the imaging. The rotation position and the phase of the rotation of the rotary turret 261 are controlled by detecting the opening (not shown) formed near the outer circumference of the rotary turret 261 using the photointerrupter 264.

Also, in the circumferential direction of the rotary turret 261, a frame F0 is provided between the optical filter F1 and the optical filter F2. The frame F0 is formed of a material that does not transmit the illuminating light. For this reason, when the frame F0 is inserted into the optical path of the illuminating light L, the light amount of the illuminating light L (normal light L1 or special light L2) passing through the rotating filter portion 260 decreases, and depending on the size and position of the frame F0, light in which the normal light L1 and the special light L2 are mixed is emitted. Hereinafter, a period during which the frame F0 is inserted into the optical path of the illuminating light L will be referred to as a transition period. The illuminating light L emitted from the rotating filter portion 260 during the transition period has an unstable light amount, and therefore is not used to image the subject.

The normal light optical filter F1 is a neutral density filter that reduces the amount of the illuminating light L, but the normal light optical filter F1 may be replaced with a simple opening (having no optical filter) or a slit (having no optical filter) that also has an aperture function. The special light optical filter F2 has a spectral characteristic that is suitable for capturing a spectral image of a blood vessel structure near a surface layer (or a deep-layer blood vessel structure, a specific lesion portion, etc.), for example.

The illuminating light L (normal light L1 and special light L2) emitted by the rotating filter portion 260 is condensed on an incident end surface of an LCB (light carrying bundle) by the condensing lens 210 and is introduced into the LCB 102. According to an embodiment, the normal light L1 is preferably white light or pseudo-white light. White light is light that has a certain light intensity in the wavelength band of visible light, and pseudo-white light is light that is constituted by multiple light components having peaks of light intensity in specific wavelength bands of the visible light wavelength band. The special light L2 is light with a narrower wavelength band compared to the wavelength band of the white light or the pseudo-white light. Thus, the normal light L1 and the special light L2 have different wavelength bands. In the electronic endoscope system, imaging is performed using the normal light L1 and the special light L2 as illuminating lights for illuminating biological tissue, which is the subject, and a normal light observation image and a special light observation image are acquired. In the special light observation image, an image different from the normal light observation image can be acquired according to the absorption characteristic of the biological tissue, and therefore a characteristic portion of the biological tissue can be observed with emphasis, making it easier to find lesion portions and the like of the biological tissue. Accordingly, the spectral characteristic of the special light optical filter F2 is set according to the absorption characteristic of the biological tissue to be emphasized.

The illuminating light L (normal light L1 and special light L2) introduced into the LCB 102 is transmitted through the LCB 102, emitted from the exit end surface of the LCB 102 arranged on the leading end of the electronic endoscope 100, and illuminates the subject via a light distribution lens 104. Accordingly, the subject is alternatingly illuminated by the normal light L1 and the special light L2. The returning light from the subject illuminated by the illuminating light L forms an optical image on a light receiving surface of the solid-state imaging element 108 via an object lens 106.

The solid-state imaging element 108 is a CMOS (complementary metal-oxide semiconductor)-type image sensor having a complementary color checkered pixel arrangement. The solid-state imaging element 108 accumulates the optical images formed on the pixels on the light receiving surface as charges corresponding to light amounts, generates yellow Ye, cyan Cy, green G, and magenta Mg pixel signals, and adds, combines, and outputs the generated pixel signals of two pixels adjacent in the orthogonal direction. Note that the solid-state imaging element 108 may be equipped with a primary color filter (a Bayer array filter). Since the solid-state imaging element 108 has a complementary color-type color filter or a primary color-type color filter, the quantum efficiency QE at the light receiving positions on the light receiving surface of the solid-state imaging element 108 changes according to the wavelength.

The timing of switching between the normal light L1 and the special light L2 performed by the rotating filter portion 260 is in synchronization with the exposure timing of the solid-state imaging element 108 and the readout timing of the charges accumulated in the solid-state imaging element 108. Accordingly, the solid-state imaging element 108 alternatingly outputs pixel signals for an observation image (normal light observation image) of the subject illuminated with the normal light L1 and pixel signals for an observation image (special light observation image) of the subject illuminated with the special light L2.

The electronic endoscope 100 is detachably connected to the processor 200. A driver signal processing circuit 110 is provided in the portion at which the electronic endoscope 100 is connected to the processor 200. The image signals of the normal light observation image and the special light observation image are alternatingly input to the driver signal processing circuit 110 by the solid-state imaging element 108. The driver signal processing circuit 110 implements predetermined processing such as amplification processing or AD conversion processing on the image signals input by the solid-state imaging element 108 and outputs the resulting image signals to the upstream signal processing circuit 220 of the processor 200.

The driver signal processing circuit 110 also accesses the memory 112 and reads out unique information of the electronic endoscope 100. The unique information of the electronic endoscope 100 stored in the memory 112 includes, for example, specifications such as the pixel count and sensitivity of the solid-state imaging element 108, the frame rate at which operation is possible, the amplification factor of the amplification processing performed by the driver signal processing circuit 110, the model number of the electronic endoscope 100, and the like. The driver signal processing circuit 110 outputs the unique information read out from the memory 112 to the system controller 202.

The system controller 202 performs various types of calculation based on the unique information of the electronic endoscope 100 and generates a control signal. The system controller 202 uses the generated control signal to control the operation and timing of various types of circuits in the processor 200 such that processing suitable for the electronic endoscope 100 connected to the processor 200 is performed.

The timing controller 204 supplies a clock pulse to the driver signal processing circuit 110 in accordance with the timing control performed by the system controller 202. In accordance with the clock pulse supplied from the timing controller 204, the driver signal processing circuit 110 performs drive control of the solid-state imaging element 108 at a timing in synchronization with the frame rate of a video processed by the processor 200.

The upstream signal processing circuit 220 generates image signals by implementing predetermined signal processing such as amplification processing, color interpolation processing, matrix calculation processing, and Y/C separation processing on the image signals of the normal light observation image and the special light observation image input by the driver signal processing circuit 110, and outputs the generated image signal to a downstream signal processing circuit 230.

The downstream signal processing circuit 230 generates screen data for monitor display by processing the image signals input by the upstream signal processing circuit 220 and converts the generated screen data for monitor display into a predetermined video format. The converted video format signal is output to the monitor 300. Accordingly, the normal light observation image and the special light observation image of the subject are displayed on the display screen of the monitor 300.

Here, the exposure timing of the solid-state imaging element and the readout timing of charges (pixel signals) in a conventional electronic endoscope system will be described.

Figure 3:
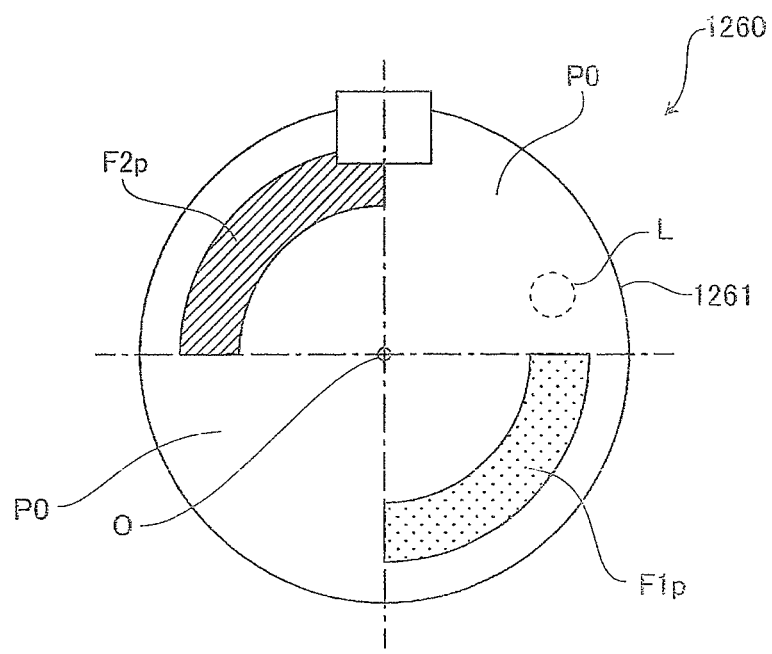
FIG. 3 is a front view of a rotating filter portion provided in a processor of a conventional electronic endoscope system.

FIG. 3 is a front view of a rotating filter portion 1260 included in a processor of a conventional electronic endoscope system. The rotating filter portion 1260 includes a rotary turret 1261. A normal light filter F1p and a special light filter F2p are arranged side by side sequentially in the circumferential direction on the rotary turret 1261. The optical filters are fan-shaped with central angles of about 90 degrees, and are arranged at positions with rotational symmetry with respect to the rotational shaft O. Also, regions P0 of the rotary turret 1261 in which the filters are not provided are light blocking regions that block the illuminating light. For this reason, by rotating the rotary turret 1261, illumination of the normal light, non-illumination, illumination of the special light, and non-illumination are switched between at a predetermined frame rate (in the present conventional example, 1/60 of a second).

Figure 4:
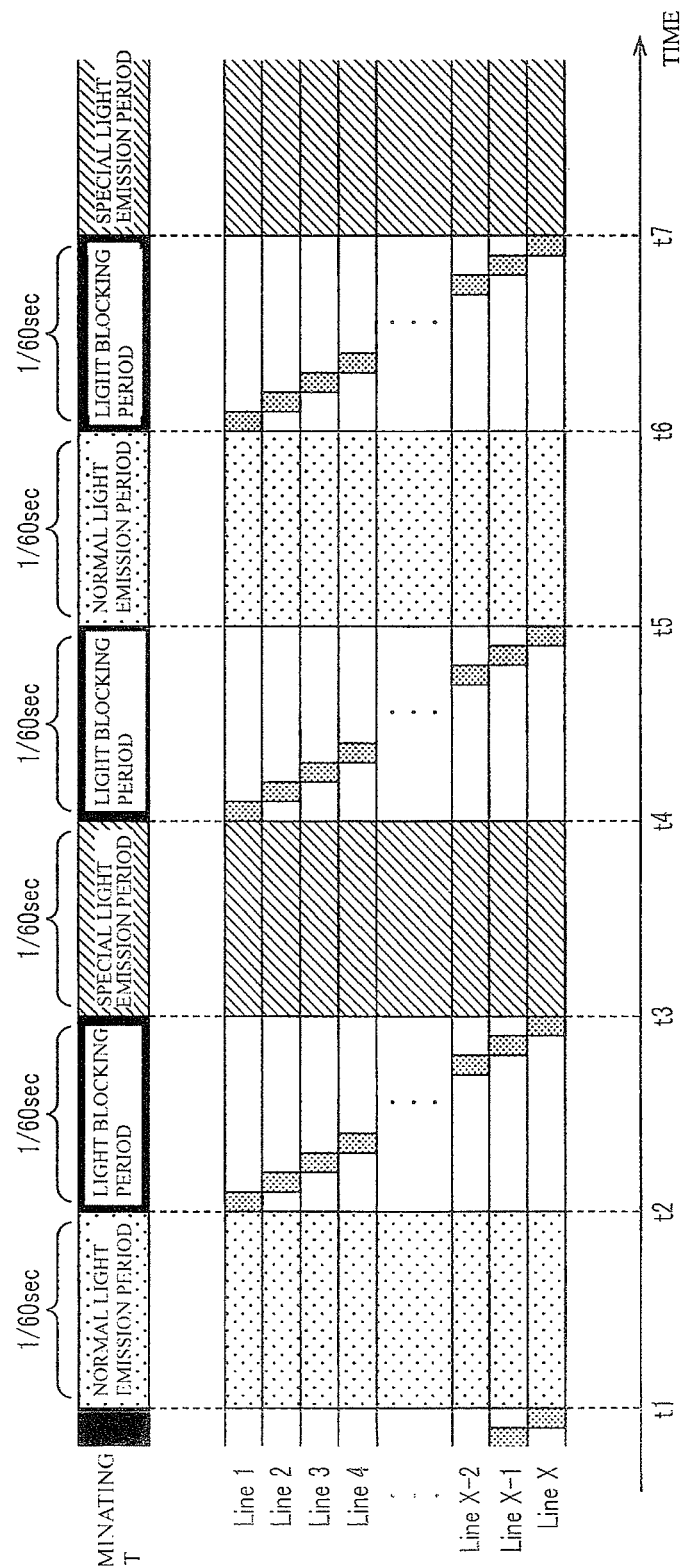
FIG. 4 is a diagram for illustrating exposure timings for a solid-state imaging element and pixel signal readout timings in the conventional electronic endoscope system.

FIG. 4 is a diagram for illustrating exposure timings of a solid-state imaging element and readout timings of charges (pixel signals) at a time of displaying a normal light observation image and a special light observation image side by side on one screen, in a conventional electronic endoscope system. The solid-state imaging element is a CMOS-type image sensor and employs a rolling shutter method for readout of pixel signals.

Multiple pixels are arranged side by side in one line and multiple lines of pixels are arranged side by side on the light receiving surface of the solid-state imaging element. The pixel signals are collectively read out line by line. FIG. 4 shows the exposure times and readout times of the lines in the case where it is envisioned that the solid-state imaging element includes pixels in X lines Line 1 to Line X.

The exposure timing of the solid-state imaging element and the readout timing of the pixel signals are synchronized with the rotation of the rotary turret 1261. Specifically, at time t1, emission of the normal light is started, and exposure of all of the pixels of the solid-state imaging element is started. The exposure of all of the pixels is performed for 1/60 of a second until time t2. At time t2, the illuminating light is blocked by the light blocking plate P0, and the readout of the charges accumulated in the pixels is performed sequentially line by line between times t1 and t2. Specifically, the readout of the pixel signals is performed sequentially starting from the line with the smallest line number, while shifting the time. The time for reading out the pixel signals from all of the pixels is 1/60 of a second. At time t3, the emission of the special light is started, and the exposure of all of the pixels of the solid-state imaging element is started. The exposure of all of the pixels is performed for 1/60 of a second from time t3 to time t4. At time t4, the illuminating light is blocked and the readout of the charges accumulated in the pixels is performed sequentially line by line in the period from time t3 to time t4.

Thus, by blocking the emission of the illuminating light to the subject during the period of reading out the pixel signals of the subject illuminated by one illuminating light of the normal light and the special light, the information of the subject illuminated by the other illuminating light is prevented from being mixed into the pixel signals and the normal light observation image and the special light observation image are displayed on the monitor 300 at 15 fps (frames per second).

Note that the normal light and the special light have different spectral characteristics and light amounts, and therefore a difference occurs in the illumination level of the subject illuminated by the normal light and the illumination level of the subject illuminated by the special light. However, with the conventional electronic endoscope system, the exposure time of the solid-state imaging element when the normal light is emitted and the exposure time of the solid-state imaging element when the special light is emitted are the same. Also, the normal light and the special light are switched rapidly every 1/30 of a second, and therefore the aperture value of the aperture cannot be adjusted according to the illumination level of the subject, which changes rapidly. As a result, a difference occurs in the amounts of charge accumulated in the solid-state imaging element when the normal light is being emitted and when the special light is being illuminated. For this reason, when the aperture value is adjusted such that any one subject image has the correct exposure, there have been cases where the other subject becomes overexposed or underexposed. If underexposure occurs, the image can be given the correct brightness through image processing using the amplification factor, but the noise will also be amplified, which is not preferable.

In view of this, the electronic endoscope system 1 according to the present embodiment is suitably configured to suppress a case in which the subject image becomes overexposed or underexposed in the conventional electronic endoscope system.

Figure 5:
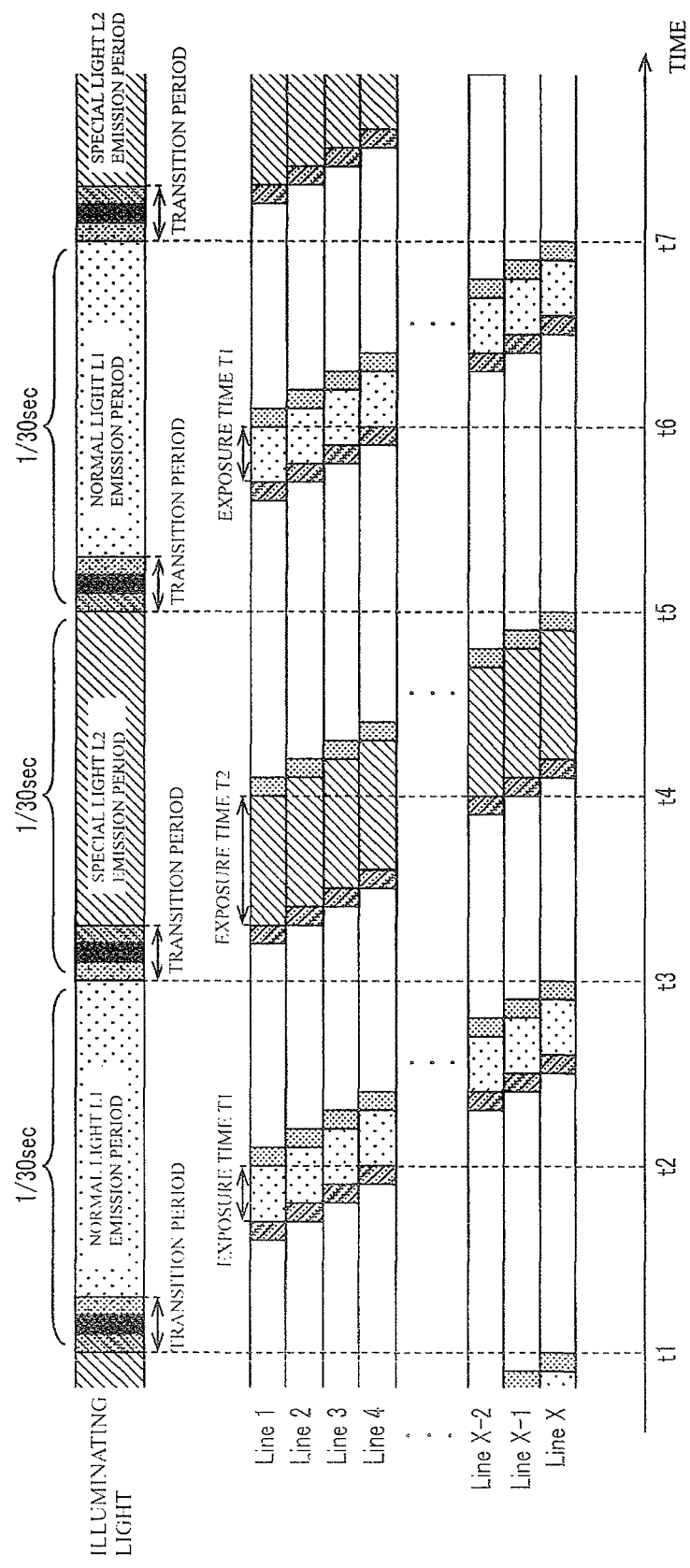
FIG. 5 is a diagram for illustrating discard timings and charge readout timings of the solid-state imaging element used in the processor according to an embodiment of the present invention.

FIG. 5 is a diagram for illustrating discard timings and readout timings of charges of pixels included in the solid-state imaging element 108 when displaying the normal light observation image and the special light observation image side by side on one screen in the present embodiment.

Multiple pixels are arranged side by side in one line and multiple lines of pixels are arranged side by side on the light receiving surface of the solid-state imaging element 108. The pixel signals are collectively read out line by line. In the embodiment shown in FIG. 5, the solid-state imaging element 108 has X lines in which multiple pixels are arranged. FIG. 5 shows the discard timings and readout timings of charges of the lines Line 1 to Line X. Discarding the charges means resetting the noise accumulation charges that are irrelevant to the captured image.

In the present embodiment, the normal light L1 and the special light L2 are alternatingly emitted to the subject every 1/30 of a second. The emission time for which the normal light L1 is continuously emitted to the subject and the emission time for which the special light L2 is continuously emitted to the subject are each 1/30 of a second, including the transition time of the illuminating light L.

The solid-state imaging element 108 is alternatingly exposed for a certain amount of time in the emission period of the normal light L1 and the emission period of the special light L2 and outputs the accumulated charges as pixel signals. Accordingly, the normal light observation image and the special light observation image can be captured at approximately the same time.

In the present embodiment, the light amount, or in other words, the light intensity of the normal light L1 is greater than the light amount, or in other words, the light intensity of the special light L2. For this reason, when the exposure time of the solid-state imaging element 108 is adjusted such that the exposure of one of the normal light observation image and the special light observation image becomes optimal, the other observation image becomes overexposed or underexposed. For example, when the exposure time is adjusted such that the exposure of the normal light observation image is optimal, the special light observation image becomes a dark image with insufficient exposure. In view of this, the solid-state imaging element 108 is subjected to drive control such that both the normal light observation image and the special light observation image have the correct exposure. Here, the light amounts, or in other words, the light intensities, refer to values obtained by integrating the spectral intensity distributions of the lights along the wavelength.

As shown in FIG. 5, the exposure time T1 of the solid-state imaging element 108 during the emission period of the normal light L1 and the exposure time T2 of the solid-state imaging element 108 during the emission period of the special light L2 are different. The exposure times are set according to the light amounts of the normal light L1 and the special light L2. Specifically, when the light amount of the normal light L1 is set to R1 and the light amount of the special light L2 is set to R2, the exposure times T1 and T2 are set such that $T1 \times R1 = T2 \times R2$. Accordingly, the exposure amount of the solid-state imaging element 108 during the emission period of the normal light L1 and the exposure amount of the solid-state imaging element 108 during the emission period of the special light L2 are approximately the same. Note that the light amount R1 is a time-integrated amount of luminous flux per unit time of the normal light L1 emitted to the subject. Note that the light amount R2 is a time-integrated amount of luminous flux per unit time of the special light L2 emitted to the subject. Accordingly, R1 and R2 correspond also to the light intensities of the normal light L1 and the special light L2. Note that with the light amounts R1 and R2, if the type of the illuminating light L, such as the normal light L1 or the special light L2, is known, its light amount is also known. According to an embodiment, association information obtained by associating the type of illuminating light with its light amount in advance is stored in the memory 23 in advance, and the information on the illuminating light L emitted from the processor 200 (the types of the normal light L1 and special light L2) is known, and therefore the light amounts R1 and R2 can be acquired using this information and the association information stored in the memory 23.

Also, the SN ratio of the pixel signals output from the solid-state imaging element 108 normally improves the greater the exposure amount is. For this reason, in an embodiment, it is preferable that the exposure time T2 for the period during which the special light L2, which has a small light amount, is emitted is set to be as long as possible. Here, the period during which the special light L2 is emitted is a period obtained by subtracting the transition period from 1/30 of a second. When the exposure time T2 is set, the exposure time T2 during the emission period of the normal light L1 is set to T1=T2×(R2/R1).

In the present embodiment, the pixels in each line are read out every 1/30 of a second using a rolling shutter method. For this reason, the exposure times T1 and T2 are adjusted according to the exposure start times instead of the readout times (exposure end times). In the present embodiment, as shown in FIG. 5, processing for discarding the charges of the pixels, or in other words, resetting of the noise accumulation charges is performed such that the exposure times T1 and T2 are set values. The time when the discard processing ends is the exposure start time, and the time from the exposure start time to when the charge readout processing is performed is the exposure time.

In FIG. 5, in the period from time t1 to time t3, the illuminating light L transitions from the special light L2 to the normal light L1 and thereafter the normal light L1 is emitted to the subject. Thereafter, the charges accumulated in the pixels are sequentially discarded line by line. Next, the charges accumulated at the timing when the exposure time of the pixels is T1 are read out line by line and are output to the driver signal processing circuit 110. In the present embodiment, the amount of time it takes for the readout of the charges of all of the pixels is 1/60 of a second, from time t2 to time t3. The timings of performing the discard processing on the charges are set by counting backward from the charge readout timings such that the exposure time is T1.

In the period from time t3 to time t5, the illuminating light L transitions from the normal light L1 to the special light L2, and thereafter the special light L2 is emitted to the subject. Thereafter, the charges accumulated in the pixels are sequentially discarded line by line. Here, the timing at which the charge discard processing is started is set such that the exposure of the pixels in Line 1 is started immediately after the period of transitioning from the normal light L1 to the special light L2 ends. Accordingly, the exposure time T2 of the special light L2 can be made longer. Next, the charges accumulated at the timing when the exposure time of the pixel is T2 are read out line by line and are output to the driver signal processing circuit 110.

Thus, in the present embodiment, the exposure time T1 of the solid-state imaging element 108 during emission of the normal light L1 is set to be shorter than the exposure time T2 during emission of the special light L2. Accordingly, if the light amount, or in other words, the light intensity of the normal light L1 is greater than the light amount, or in other words, the light intensity of the special light L2, the difference between the amounts of charge accumulated in the solid-state imaging element 108 can be made smaller. For this reason, the subject images with the correct exposure are obtained at both the time when the normal light L1 is emitted and the time when the special light L2 is emitted.

Also, in the present embodiment, the processing of reading out the charges of the pixels is performed every 1/30 of a second, and the charge discard processing is performed at timings corresponding to the exposure times T1 and T2, but the present embodiment is not limited to this. It is sufficient that the exposure times T1 and T2 of the solid-state imaging element 108 do not include the transition periods of the illuminating light L, and the charge readout processing need not be performed at a certain interval. For example, the charge discard processing may be performed at the timing when the period of transitioning from the normal light. L1 to the special light L2 ends, and at the timing when the period of transitioning from the special light. L2 to the normal light L1 ends. In this case, the charge discard processing is performed every 1/30 of a second, and the charge readout processing is performed at timings corresponding to the exposure times T1 and T2.

According to an embodiment, the solid-state imaging element 108 is configured to read out the charges at the light receiving position while shifting the timings of starting and ending exposure at the light receiving positions on the light receiving surface of the solid-state imaging element 108, and the light amount, or in other words, the light intensity of the normal light L1 (first illuminating light) is greater than the light amount, or in other words, the light intensity of the special light L2 (second illuminating light). In this case, the exposure time T2 of the special light L2 is preferably less than or equal to a reference time obtained by dividing the emission time of the special light L2 (second illuminating light) by the number of instances of reading out the charges at all light receiving positions, and is preferably greater than or equal to a time obtained by subtracting the time for reading out the charges and the reset time for resetting the noise accumulation charges prior to exposure of the light receiving position from the reference time. Thus, by ensuring the exposure time T2 of the special light L2 with the low light intensity to the greatest extent possible, it is possible to reduce the difference in the amounts of charges accumulated in the solid-state imaging element 108 between the special light L2 with a weak light intensity and the normal light L1 with a strong light intensity.

Also, according to an embodiment, the minimum amount of time for shifting the light receiving position, for example, the shift time between adjacent lines, in the timings of starting and ending the exposure of the solid-state imaging element 108 is preferably equal to the reset time for resetting the noise accumulation charge. Accordingly, the exposure time T2 can be extended during the limited emission period.

Also, as shown in FIG. 5, the normal light L1 (first illuminating light) and the special light L2 (second illuminating light) have transition periods in which the light intensity gradually increases along with the time from the start of emission, before the light intensity becomes constant. In this case, it is preferable that the period of resetting the noise accumulation charges (charge discard processing), performed before charge readout, which is performed first in the emission time of the special light L2, is in the transition period. Accordingly, the exposure time T2 can be extended during the limited emission period.

In the above-described embodiment, the exposure time T1 of the normal light L1 and the exposure time T2 of the special light L2 are set such that T1×R1=T2×R2 is satisfied, but the embodiment of the present invention is not limited thereto. According to an embodiment, the exposure times T1 and T2 may be set using the gain of the amplification processing on the image signal, in addition to the light amounts R1 and R2. Specifically, the exposure times T1 and T2 are set such that T1×R1×G1=T2×R2×G2 is satisfied. Here, G1 is the gain of the amplification processing on the image signal of the normal light observation image. Also, G2 is the gain of the amplification processing on the image signal of the special light observation image.

The image signals are amplified by the driver signal processing circuit 110 and the upstream signal processing circuit 220. The driver signal processing circuit 110 implements amplification processing on the analog pixel signals output from the solid-state imaging element 108. Also, the upstream signal processing circuit 220 implements amplification processing on the digital pixel signals resulting from AD conversion. The system controller 202 acquires the gain of the amplification processing performed by the driver signal processing circuit 110 and the gain of the amplification processing performed by the upstream signal processing circuit 220 and calculates the gains G1 and G2. The gains G1 and G2 are the products of the gain of the amplification processing performed by the driver signal processing circuit 110 and the gain of the amplification processing performed by the upstream signal processing circuit 220. According to an embodiment, the gain of the amplification processing is switched between G1 and G2 each time the illuminating light L is switched between the normal light L1 and the special light L2. Note that in response to the switching of the illuminating light L, either one of the gain of the amplification processing performed by the driver signal processing circuit 110 and the gain of the amplification processing performed by the upstream signal processing circuit 220 may be switched to, or both may be switched between. Also, the amplification processing performed on the image signal may be implemented by only one of the driver signal processing circuit 110 and the upstream signal processing circuit 220.

For example, if the light amount R2 of the special light L2 is smaller than the light amount R1 of the special light L1, the exposure time T2 becomes longer when the exposure times T1 and T2 are set such that T1×R1=T2×R2. Since blurring is more likely to occur in the captured image the longer the exposure time is, if there is a large difference between the light amount R1 and the light amount R2, there is a possibility that the observation image captured using the special light L2 will become difficult to see due to blurring. However, if the exposure times T1 and T2 are set such that T1×R1×G1=T2×R2×G2 is satisfied, the exposure time T2 is set to be shorter due to the gain G2 being made larger. Accordingly, an observation image with suppressed blurring can be obtained. Note that in this case, the exposure time T1 and the exposure time T2 may be set to the same length, or may be set to different lengths.

Also, if the gains G1 and G2 are made too large, the noise included in the image signals is also amplified, and there is a possibility that the observation image will become difficult to see. Furthermore, as described above, if the exposure times T1 and T2 are made too long, there is a possibility that blurring will occur in the observation image. For this reason, in the present Modified Example 1, an upper limit value may be set for one or both of the exposure times (T1, T2) and the gains (G1, G2).

Figure 6:
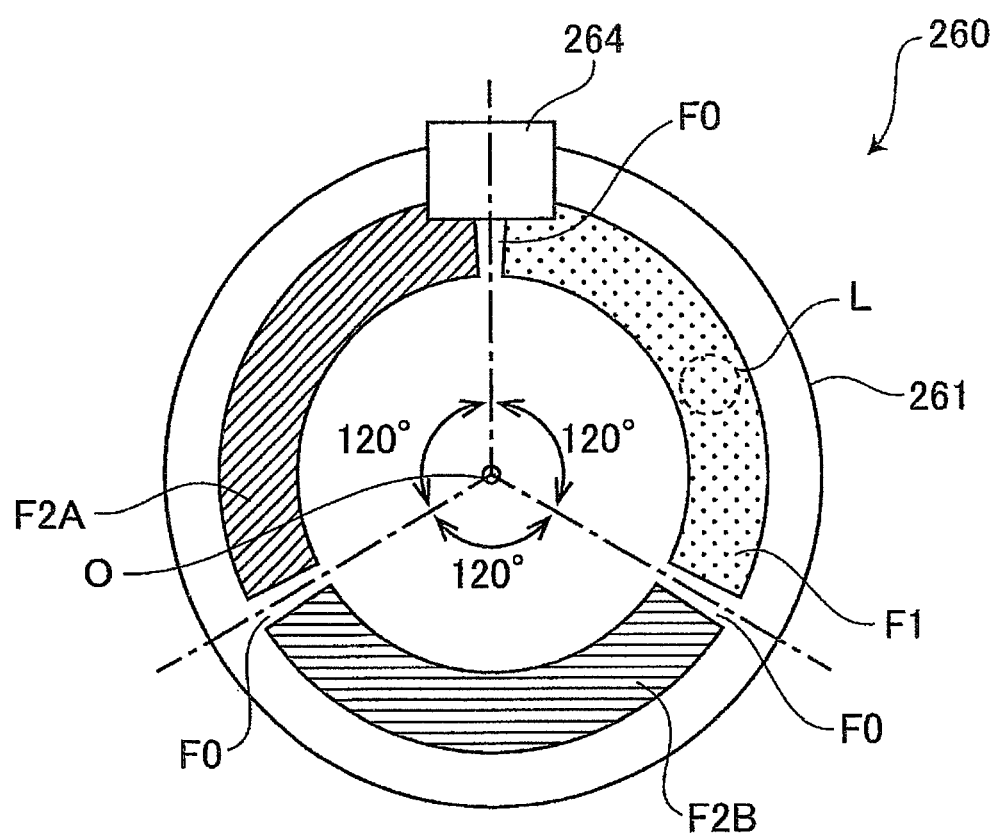
FIG. 6 is a front view of the rotating filter portion provided in the processor according to an embodiment of the present invention.

In the above-described embodiment, the illuminating light L is alternatingly switched between the normal light L1 and the special light L2, but the embodiment of the present invention is not limited thereto. According to an embodiment, the illuminating light L may be switched sequentially between three or more types of light. FIG. 6 is a front view of a rotating filter portion 260 of an embodiment. In the rotating filter portion 260, a normal light optical filter F1, a special light optical filter F2A, and a special light optical filter F2B are arranged side by side in the circumferential direction. The optical filters F1, F2A, and F2B are fan-shaped and are arranged in approximately 120-degree angle ranges around a rotational shaft O. The special light optical filter F2A and the special light optical filter F2B have mutually different spectral transmission characteristics. Due to the optical filters F1, F2A, and F2B being sequentially inserted into the optical path of the illuminating light L, the illuminating light L introduced by the lamp 208 is filtered with the optical filters and the three types of illuminating light with different spectra (normal light L1, special light L2A, and special light L2B) are sequentially emitted at timings in synchronization with the imaging.

According to an embodiment, the normal light L1, the special light L2A, and the special light L2B are sequentially emitted to the subject every ⅓₀ of a second. The emission time for which the normal light L1 is continuously emitted to the subject, the emission time for which the special light L2A is continuously emitted to the subject, and the emission time for which the special light L2B is emitted to the subject are each ⅓₀ of a second, including the transition time of the illuminating light L. The solid-state imaging element 108 is exposed to light for the emission time of the illuminating light L and outputs the accumulated charges as the pixel signals. Accordingly, the normal light observation image, the special light observation image A using the special light L2A, and the special light observation image B using the special light L2B can be captured at the same time.

In the above-described embodiment, the light amount of the normal light L1 is larger than the light amount of the special light L2A. Also, the light amount of the special light L2A is greater than the light amount of the special light L2B. For this reason, the exposure time of the solid-state imaging element 108 in the emission periods of the illuminating light L is adjusted such that the exposures of three observation images, namely the normal light observation image, the special light observation image A, and the special light observation image B are correct.

Figure 7:
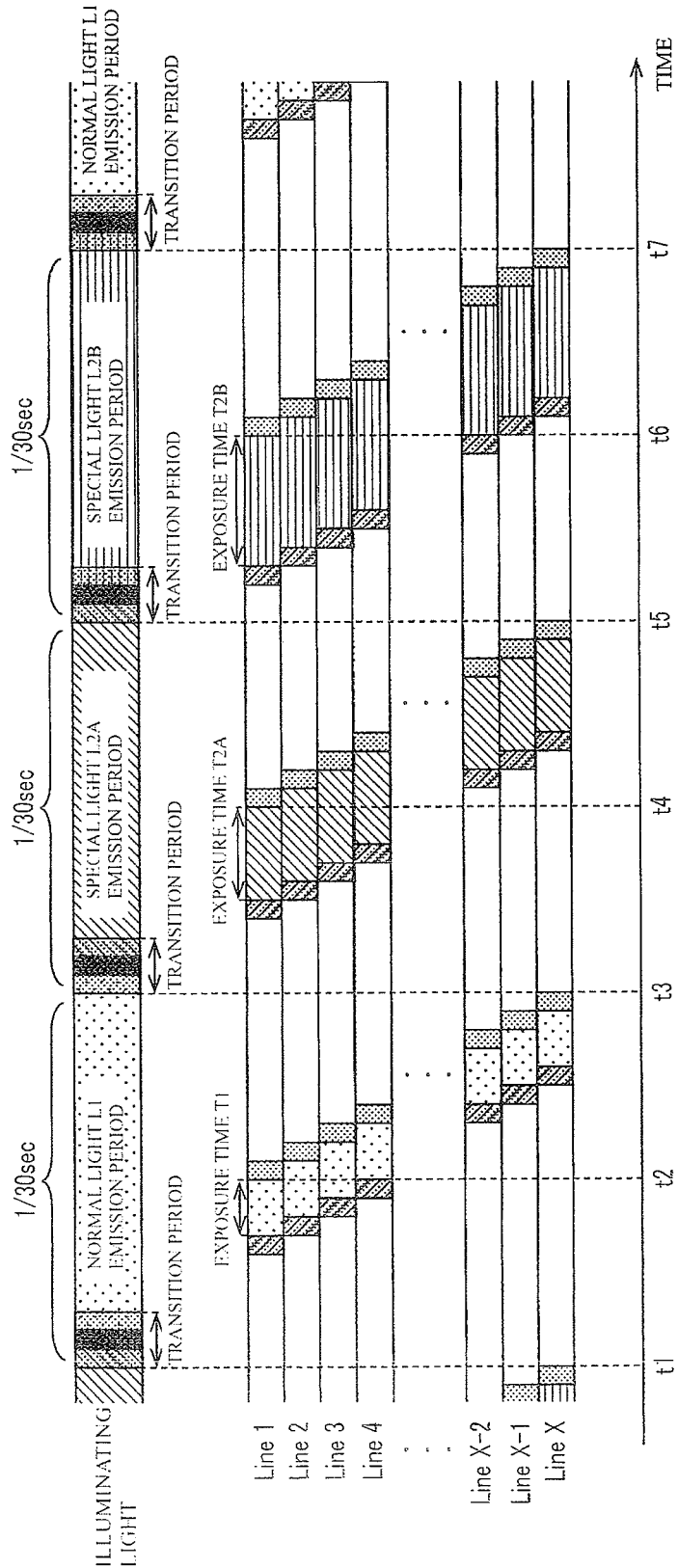
FIG. 7 is a diagram for illustrating discard timings and charge readout timings of the solid-state imaging element used in the processor according to an embodiment of the present invention.

FIG. 7 is a diagram for illustrating discard timings and readout timings of the charges of the pixels included in the solid-state imaging element 108, in emission using the normal light L1, the special light L2A, and the special light L2B.

As shown in FIG. 7, the exposure time T1 of the solid-state imaging element 108 in the emission period of the normal light L1, the exposure time T2A of the solid-state imaging element 108 in the emission period of the special light L2A, and the exposure time T2B of the solid-state imaging element 108 in the emission period of the special light L2B are different. The exposure times T1, T2A, and T2B are set according to the light amounts of the normal light L1, the special light L2A, and the special light L2B. Specifically, when the light amount of the normal light L1 is R1, the light amount of the special light L2A is R2A, and the light amount of the special light L2B is R2B, the exposure times T1, T2A, and T2B are set such that T1×R1=T2A×R2A=T2B×R2B. Here, the light amount R1 is a time-integrated amount of luminous flux per unit time of the normal light L1 emitted to the subject. Also, the light amount R2A is a time-integrated amount of luminous flux per unit time of the special light L2A emitted to the subject. Also, the light amount R2B is a time-integrated amount of luminous flux per unit time of the special light L2B emitted to the subject. Thus, the exposures of the three observation images, namely the normal light observation image, the special light observation image A, and the special light observation image B are correct.

Note that in the case shown in FIG. 7 as well, the exposure times T1, T2A, and T2B may be set using the gains for the image signals, in addition to the light amounts R1, R2A, and R2B. Specifically, the exposure times T1, T2A, and T2B may be set such that T1×R1×G1=T2A×R2A×G2A=T2B×R2B×G2B is satisfied. Here, G1 is the gain of the amplification processing on the image signal of the normal light observation image. Also, G2A is the gain of the amplification processing on the image signal of the special light observation image A. Also, G2B is the gain of the amplification processing on the image signal of the special light observation image B. In this manner, by setting the exposure times T1, T2A, and T2B using the gains of the image signals, the exposure times can be prevented from becoming too long and blurring can be prevented from occurring in the observation images.

In all of the above-described embodiments, it was described that the normal light L1 and the special light L2 (or the special light L2A and the special light L2B) have a difference in light amount, or in other words, light intensity, and the exposure times are set in correspondence to the difference, but it is preferable that the exposure time is set with consideration given to the quantum efficiency of the solid-state imaging element 108 in order to accurately realize the correct exposure of the subject.

FIGS. 8A to 8E are diagrams illustrating calculation amounts K1 and K2 that are used by the processor according to an embodiment. The calculation amounts K1 and K2 are amounts used instead of the above-described light amounts R1 and R2, with consideration given to the quantum efficiency of the solid-state imaging element 108.

Figure 8A:
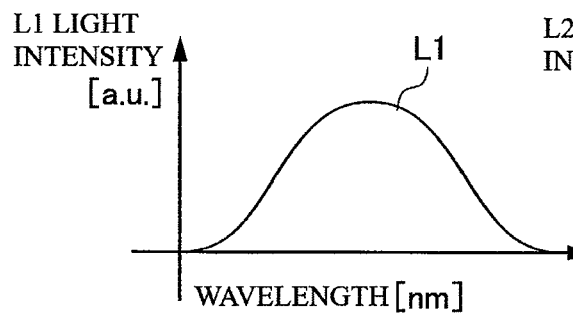
FIGS. 8A to 8E are diagrams illustrating calculation amounts K1 and K2 to be used in the processor according to an embodiment of the present invention.
Figure 8B:
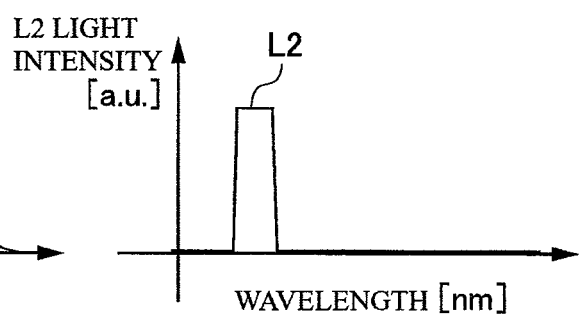
Figure 8C:
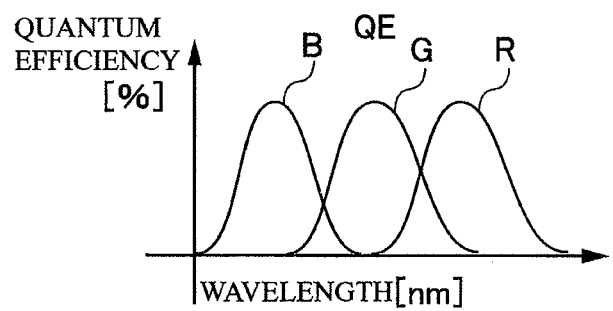
Figure 8D:
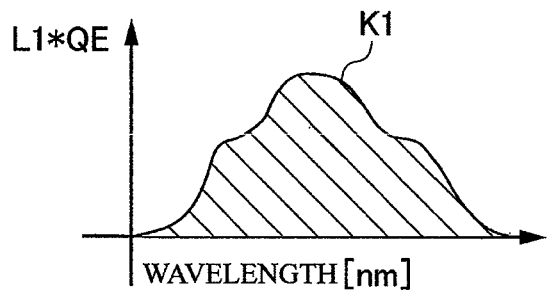
Figure 8E:
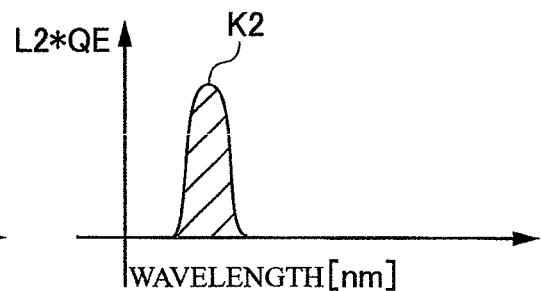

It is assumed that the normal light L1 and the special light L2 have light intensity distributions such as those shown in FIGS. 8A and 8B, and have characteristics of quantum efficiency QE of the solid-state imaging element 108 as shown in FIG. 8C. Note that the quantum efficiency QE refers to the efficiency with which photons incident on the photoelectric surface (light receiving surface) are converted into electrons, and for example, significantly depends on the wavelength characteristic of the photoelectric conversion of the photoelectric surface (light receiving surface) of the solid-state imaging element 108 and the transmissivity characteristic of the color filter (e.g., primary color filter) provided on the front surface of the photoelectric surface (light receiving surface). Accordingly, as shown in FIGS. 8D and 8E, the amounts resulting from integrating the products of the light intensity distributions shown in FIGS. 8A and 8B and the distribution of the quantum efficiency of the solid-state imaging element 108 in the ranges of the wavelength bands are set as the calculation values K1 and K2, and the calculation values K1 and K2 are preferably used instead of the light amounts R1 and R2. That is, the calculation amounts K1 and K2 are amounts obtained by integrating the products of the light intensity distributions in the wavelength bands of the normal light L1 and the special light L2 and the distribution of the quantum efficiency of the solid-state imaging element 108 in the wavelength band of the normal light L1 and the special light L2, in the ranges of the wavelength bands.

Note that the information on the characteristic of the quantum efficiency QE is included in the unique information of the electronic endoscope 100 as the information on the solid-state imaging element 108 and is stored in the memory 112. When the electronic endoscope 100 is connected to the processor 200, the information on the characteristic of the quantum efficiency QE is acquired by being read out from the driver signal processing circuit 110 and is output to the system controller 110.

According to an embodiment, it is preferable that the exposure time T1 of the solid-state imaging element 108 when the normal light L1 (first illuminating light) is being emitted to the subject and the exposure time T2 of the solid-state imaging element 108 when the special light L2 (second illuminating light) is being emitted to the subject are controlled based on the above-described calculation amount K1 relating to the normal light L1 in the wavelength band of the normal light L1 and the above-described calculation amount K2 relating to the special light L2 in the wavelength band of the special light L2.

In this case, the exposure times T1 and T2 are preferably controlled such that $T1 \times K1 = T2 \times K2$ is satisfied. Furthermore, when the gains (amplification factors) implemented on the image signals of the subject to which the normal light L1 (first illuminating light) and the special light L2 (second illumination light) were emitted are set as G1 and G2 respectively, the exposure times T1 and T2 are preferably controlled such that $T1 \times K1 \times G1 = T2 \times K2 \times G2$ is satisfied. According to an embodiment, the exposure time T1 is preferably set based on the exposure time T2.

In the above-described embodiment, due to the fact that there is a possibility that the observation image will become difficult to see due to blurring if the exposure time is made longer in the emission period of the special light L2 and the like, the exposure time is suppressed from being made longer, and the amplification factor, that is, the gain in the amplification processing is adjusted instead. In this case, after the exposure time is set in advance, in order to set the gain, the calculation amounts K1 and K2 can be used instead of the light amounts R1 and R2. According to an embodiment, the gain implemented on the image signal of the subject to which one of the normal light L1 (first illuminating light) and the special light L2 (second illuminating light) was emitted is preferably controlled based on the gain (amplification factor) implemented on the image signal of the subject to which the other was emitted, the above-described calculation amount K1 and the above-described calculation amount K2, and the exposure time of the solid-state imaging element 108 in the emission period of the normal light L1 and the special light L2.

In this case, if the gains (amplification factors) implemented on the image signals of the subject to which the normal light L1 (first illuminating light) and the special light L2 (second illuminating light) are emitted are defined as G3 and G4 respectively and the exposure times of the solid-state imaging element 108 when the normal light L1 (first illuminating light) and the special light L2 are being emitted are defined as T3 and T4 respectively, the amplification factors G3 and G4 are preferably controlled based on $G3 \times T3 \times K1 = G4 \times T4 \times K2$. According to an embodiment, the amplification factor G4 is preferably set based on the known amplification factor G3.

In the above-described embodiment, the exposure time T1 in the emission period of the normal light L1 is set to $T1=T2 \times (R2/R1)$. However, in this case, the exposure cannot be performed correctly in some cases since no consideration is given to the quantum efficiency of the solid-state imaging element 108. In this case, the gains (amplification factors) implemented on the image signals of the subject to which the normal light L1 (first illuminating light) and the special light L2 (second illuminating light) were emitted can be adjusted with consideration given to the quantum efficiency. Thus, according to an embodiment, it is also preferable that the amplification factor implemented on the image signal of the subject to which one of the normal light L1 (first illuminating light) and the special light L2 (second illuminating light) was emitted is controlled based on the above-described calculated amount K1, the above-described calculated amount K2, and the set exposure times T1 and T2.

According to an embodiment, if the amplification factors implemented to the image signals of the subject to which the normal light L1 (first illuminating light) and the special light L2 (second illuminating light) were emitted are defined as G3 and G4 respectively, and the exposure times of the solid-state imaging element 108 when the normal light L1 (first illuminating light) and the special light L2 (second illuminating light) are being emitted are defined as T3 and T4 respectively, the amplification factors G3 and G4 are preferably controlled based on G3×T3×K1=G4×T4×K2. According to an embodiment, the amplification factor G4 is preferably set based on the known amplification factor G3.

Instead of the above-described embodiment in which the calculation amounts K1 and K2 are used to control the exposure times T1 and T2 and the amplification factors G1 and G2 or the amplification factors G3 and G4, it is also possible to use average quantum efficiencies AQE1 and AQE2 to control the exposure times T1 and T2 and the amplification factors G1 and G2, or the amplification factors G3 and G4. For example, since the wavelength band of the normal light L1 (first illuminating light) and the special light L2 (second illuminating light) are known in advance, it is also possible to calculate the average quantum efficiency of the quantum efficiency QE in the wavelength band and use it instead of the calculation amounts K1 and K2. In this case, the calculation amounts K1 and K2 do not need to be calculated in advance, and the processing can also be simplified.

According to an embodiment, the average quantum efficiencies AQE1 and AQE2 are preferably obtained in advance as AQE1=K1/R1 and AQE2=K2/R2. Since the types of the illuminating light L (normal light, special light) emitted by the processor 200 are known in advance, the light intensity distribution of the illuminating light L is information that can be acquired. Also, the characteristic of the quantum efficiency QE (characteristic shown in FIG. 8C) is also information that can be acquired based on the information of the solid-state imaging element 108 included in the unique information of the electronic endoscope 100 connected to the processor 200. Accordingly, the average quantum efficiencies AQE1 and AQE2 calculated using the calculation amounts K1 and K2 and R1 and R2 obtained based on these acquired pieces of information can be acquired and used when adjusting the exposure time and the later-described gain (amplification factor). These average quantum efficiencies AQE1 and AQE2 can be acquired without performing an arithmetic operation using the system controller 202 or the like. For example, association information in which a combination of information on the types the illuminating light L and the quantum efficiency QE included in the unique information of the electronic endoscope 100 and the average quantum efficiency are associated can be stored in advance in the memory 212, and the value of the average quantum efficiency can be set by referencing the association information when the electronic endoscope 100 is connected to the processor 200.

According to an embodiment, the exposure time T1 and the exposure time T2 are preferably controlled such that T1×R1×AQE1=T2×R2×AQE2 is satisfied instead of T1×K1=T2×K2. According to an embodiment, the exposure time T1 is preferably set based on the known exposure time T2.

Also, according to an embodiment, when the gains (amplification factors) implemented on the image signals of the subject to which the normal light L1 (first illuminating light) and the special light L2 (second illuminating light) were emitted are set as G1 and G2 respectively, the exposure times T1 and T2 are preferably adjusted such that T1×R1×AQE1×G1=T2×R2×AQE2×G2 is satisfied.

The information on the average quantum efficiency is set for each wavelength band of the normal light L1 and the special light L2 set in advance as the information on the solid-state imaging element 108, and the information is included in the unique information of the electronic endoscope 100 and stored in the memory 112. When the electronic endoscope 100 is connected to the processor 200, the information on the characteristic of the quantum efficiency QE is acquired by being read out from the driver signal processing circuit 110 and is output to the system controller 110.

In all of the above-described embodiments, the exposure times and the amplification factors (gains) are controlled using the information on the light amounts of the normal light L1, the special light L2, and the like, but according to an embodiment, it is also preferable that the above-described control is not performed, and the exposure times and the amplification factors are fixed at values controlled such that the correct exposure conditions are satisfied.

For example, the exposure time T1 of the solid-state imaging element 108 when the normal light L1 (first illuminating light) is being emitted to the subject and the exposure time T2 of the solid-state imaging element 108 when the special light L2 (second illuminating light) is being emitted to the subject are preferably set such that T1×K1=T2×K2 is satisfied.

In the above-described embodiment, the light amounts R1, R2, and R3 are time-integrated amounts of luminous flux per unit time of the illuminating light. In an embodiment, when an image signal is to be generated from the photoelectric conversion performed by the solid-state imaging element 108, the image signal is generated by performing logarithmic conversion on the output signals from the solid-state imaging element 108 in some cases. Accordingly, in an embodiment, regarding the light amounts R1, R2, and R3, time-integrated amounts of luminous flux per unit time of the illuminating light, which are amounts resulting from logarithmic conversion, are preferably used as the light amounts R1, R2, and R3. Also, regarding the above-described calculation amounts K1 and K2 as well, in an embodiment, amounts obtained by integrating the product of the light intensity distribution in the wavelength band of the illuminating light and the distribution of the quantum efficiency of the solid-state imaging element 108 in the range of the wavelength band, the amounts resulting from logarithmic conversion, are preferably used as the calculation amounts K1 and K2. Accordingly, the time-integrated amounts of luminous flux per unit time of the illuminating light, and the amounts obtained by integrating the product of the light intensity distribution in the wavelength band of the illuminating light and the distribution of the quantum efficiency of the solid-state imaging element 108 also include amounts resulting from logarithmic conversion.

Illustrative embodiments of the present invention have been described above. The embodiment of the present invention is not limited to the above description, and various modifications are possible within the scope of the technical idea of the present invention. For example, content obtained by combining the embodiments and the like specified illustratively in the specification and obvious embodiments or the like as appropriate is also encompassed in the embodiments of the present invention.

REFERENCE SIGNS LIST

1 Electronic endoscope system
100 Electronic endoscope
102 LCB
104 Light distribution lens
106 Object lens 108 Solid-state imaging element
110 Driver signal processing circuit
112 Memory
200 Processor
202 System controller
204 Timing controller
206 Lamp power source igniter
208 Lamp
210 Condensing lens
212 Memory
214 Operation panel
220 Upstream signal processing circuit
230 Downstream signal processing circuit
260 Rotating filter portion
261 Rotary turret.
F1 Normal light optical filter
F2 Special light optical filter
F2A Special light optical filter
F2B Special light optical filter
F0 Frame
262 DC motor
263 Driver
264 Photointerrupter
1260 Rotating filter portion
1261 Rotary turret
F1p Normal light optical filter
F2p Special light optical filter
P0 Light blocking plate

The invention claimed is:

1. An electronic endoscope processor for processing image signals of a subject imaged using an imaging element, comprising:
   an illuminating light switch that alternatingly switches illuminating light to be emitted to a subject, between a first illuminating light and a second illuminating light with a different time-integrated amount of luminous flux per unit time from the first illuminating light, the first illuminating light being used to capture a first image, the second illuminating light being used to capture a second image different from the first image, the first image and the second image being alternatingly captured; and
   an imaging element control circuit that controls an exposure time of the imaging element and a charge readout timing,
   wherein the imaging element control circuit controls an exposure time T1 of the imaging element when the first illuminating light is being emitted to the subject and an exposure time T2 of the imaging element when the second illuminating light is being emitted to the subject, based on a time-integrated amount R1 of luminous flux per unit time of the first illuminating light and a time-integrated amount R2 of luminous flux per unit time of the second illuminating light,
   wherein the imaging element is configured to perform a rolling shutter method to read out the charges at the light receiving positions while shifting the timings of starting and ending exposure at the light receiving positions on the light receiving surface of the imaging element,
   wherein the first illuminating light and the second illuminating light each has a transition period in which light intensity of one of the first illuminating light and the second illuminating light decreases and the light intensity of the other of the first illuminating light and the second illuminating light increases over time from the start of emission, before the light intensity of the other of the first illuminating light and the second illuminating light becomes constant, the transition period being a period when the first illuminating light and the second illuminating light are switched,
   wherein the transition period including a period in which the first illuminating light and the second illuminating light are simultaneously emitted to the subject,
   wherein an exposure period of the imaging element with the first illuminating light and the second illuminating light excludes the transition period, and
   wherein the imaging element control circuit defines the exposure time T2 such that exposure starts and ends with the rolling shutter method, at all of the light receiving positions of the imaging element, in a period in which the light intensity of the second illuminating light stays constant, and defines the exposure time T1 so as to be shorter than the defined exposure time T2.

2. The electronic endoscope processor according to claim 1, wherein
   the imaging element control circuit adjusts the exposure time T1 and the exposure time T2 such that T1×R1=T2×R2 is satisfied.

3. The electronic endoscope processor according to claim 1, wherein
   an electronic endoscope including the imaging element is attachable to and detachable from the electronic endoscope processor,
   the imaging element control circuit acquires an amplification factor for amplification processing implemented on the image signal in at least one of the electronic endoscope and the electronic endoscope processor, and
   if the amplification factor of amplification processing implemented on the image signal of the subject to which the first light was emitted is defined as G1 and the amplification factor of amplification processing implemented on the image signal of the subject to which the second light was emitted is defined as G2, the imaging element control circuit adjusts the exposure time T1 and the exposure time T2 such that T1×R1×G1=T2×R2×G2 is satisfied.

4. The electronic endoscope processor according to claim 1, wherein
   the time for which the first illuminating light is continuously emitted to the subject and the time for which the second illuminating light is continuously emitted to the subject are equal.

5. The electronic endoscope processor according to claim 1, wherein the illuminating light switch includes:
   a light source configured to emit white light;
   a rotating plate in which a first filter for filtering the white light into the first illuminating light and a second filter for filtering the white light into the second illuminating light are arranged side by side in approximately the same angle range in a circumferential direction; and
   a rotation drive unit configured to, by rotating the rotating plate, insert the first filter into an optical path of the white light in an emission period of the first illuminating light, and insert the second filter into the optical path in an emission period of the second illuminating light.

6. The electronic endoscope processor according to claim 1, wherein
   the illuminating light switch sequentially switches the illuminating light emitted to the subject between the first illuminating light, the second illuminating light, and a third illuminating light that has a time-integrated amount of luminous flux per unit time that is different from those of the first illuminating light and the second illuminating light, and the imaging element control circuit controls the exposure time $T1$, the exposure time $T2$, and an exposure time $T3$ of the imaging element when the third illuminating light is being emitted to the subject, based on the time-integrated amount $R1$, the time-integrated amount $R2$, and a time-integrated amount $R3$ of luminous flux per unit time of the third illuminating light.

* * * * *